US010436761B2

(12) United States Patent
Jin et al.

(10) Patent No.: US 10,436,761 B2
(45) Date of Patent: Oct. 8, 2019

(54) GAS IDENTIFICATION BY MEASURING STAIN DEVELOPMENT AT MULTIPLE SPECIFIC WAVELENGTH REGIONS WITH NARROW BAND OPTICAL SENSORS

(71) Applicant: Honeywell International Inc., Morristown, NJ (US)

(72) Inventors: Peng Jin, Barlett, IL (US); Takashi Yamaguchi, Lake Forest, IL (US)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 484 days.

(21) Appl. No.: 14/704,140

(22) Filed: May 5, 2015

(65) Prior Publication Data
US 2016/0327533 A1    Nov. 10, 2016

(51) Int. Cl.
*G01N 29/24* (2006.01)
*G01N 33/00* (2006.01)
(Continued)

(52) U.S. Cl.
CPC ....... *G01N 33/0031* (2013.01); *G01N 21/643* (2013.01); *G01N 21/6428* (2013.01);
(Continued)

(58) Field of Classification Search
CPC ... G01N 2021/7759; G01N 2021/7763; G01N 2021/7773; G01N 21/6428; G01N 21/643;
(Continued)

(56) References Cited

U.S. PATENT DOCUMENTS

| 3,460,153 A | 8/1969 | White |
| 4,281,245 A * | 7/1981 | Brogardh ............... G01D 5/268 |
| | | 250/205 |

(Continued)

FOREIGN PATENT DOCUMENTS

| CN | 108027355 A | 5/2018 |
| EP | 0092246 A2 | 10/1983 |

(Continued)

OTHER PUBLICATIONS

O'Toole, Martina, and Dermot Diamond. "Absorbance based light emitting diode optical sensors and sensing devices." Sensors 8.4 (2008): 2453-2479.*

(Continued)

*Primary Examiner* — Harshad R Patel
(74) *Attorney, Agent, or Firm* — Wick Phillips Gould & Martin, LLP

(57) ABSTRACT

Systems and methods for detecting gas using a wide band light source, and at least two narrow band light sensors, wherein each sensor may be operable to detect light at a different range of wavelengths. Additionally, the gas detector device may comprise a color changing indicator operable to react with gas in the air to change color, wherein different gases may react to create different colors, and wherein the sensors detect light reflected by the color changing indicator from the wide band light source. The gas detector device may comprise a processor in communication with the at least two light sensors operable to receive detected reflected wavelength information from the light sensors, and determine the type of gas that reacted with the color changing indicator based on the color detected by the sensors, wherein each color may be associated with a different type of gas.

14 Claims, 3 Drawing Sheets

(51) Int. Cl.
  *G01N 31/22* (2006.01)
  *G01N 21/64* (2006.01)
  *G01N 21/78* (2006.01)
  *G01N 21/77* (2006.01)

(52) U.S. Cl.
  CPC .......... *G01N 21/78* (2013.01); *G01N 21/783* (2013.01); *G01N 31/223* (2013.01); *G01N 2021/7759* (2013.01); *G01N 2021/7763* (2013.01); *G01N 2021/7773* (2013.01); *G01N 2201/062* (2013.01); *G01N 2201/0621* (2013.01)

(58) Field of Classification Search
  CPC ................. G01N 21/78; G01N 21/783; G01N 2201/062; G01N 2201/0621; G01N 31/22; G01N 31/223; G01N 31/225; G01N 33/0031
  See application file for complete search history.

(56) References Cited

U.S. PATENT DOCUMENTS

| | | | | |
|---|---|---|---|---|
| 4,681,454 | A | * | 7/1987 | Breemer ............... G01J 3/46 250/205 |
| 5,098,659 | A | | 3/1992 | Yim et al. |
| 5,239,175 | A | * | 8/1993 | Jawad ................ G01N 21/255 250/205 |
| 6,328,932 | B1 | | 12/2001 | Carter et al. |
| 7,688,447 | B2 | * | 3/2010 | Shakespeare ............ G01J 3/10 356/402 |
| 7,924,338 | B2 | * | 4/2011 | Parks ................... H04N 9/045 348/311 |
| 9,110,029 | B2 | * | 8/2015 | O'Farrell ............. G01N 21/78 |
| 9,547,015 | B2 | * | 1/2017 | O'Farrell ............. G01N 21/78 |
| 2005/0037512 | A1 | | 2/2005 | Yeh et al. |
| 2005/0057365 | A1 | | 3/2005 | Qualey, III |
| 2008/0190172 | A1 | | 8/2008 | Jones |
| 2010/0024526 | A1 | | 2/2010 | Colvin, Jr. et al. |
| 2010/0221468 | A1 | | 9/2010 | Khan et al. |
| 2012/0202294 | A1 | | 8/2012 | Jin |
| 2014/0051179 | A1 | | 2/2014 | Truex et al. |

FOREIGN PATENT DOCUMENTS

| | | |
|---|---|---|
| EP | 3292403 A1 | 3/2018 |
| KR | 20180021691 A | 3/2018 |
| WO | 2016179067 A1 | 11/2016 |

OTHER PUBLICATIONS

"Optical Resolution of Photodiode Array Detectors." Waters Corporation Performance Perspectives. 2009. <http://www.waters.com/webassets/cms/library/docs/wpp09.pdf>.*
Muthu, Subramanian, Frank J. Schuurmans, and Michael D. Pashley. "Red, green, and blue LED based white light generation: issues and control." Industry Applications Conference, 2002. 37th IAS Annual Meeting. Conference Record of the. vol. 1. IEEE, 2002.*
International Application No. PCT/US2016/030365, International Search Report, dated May 9, 2016, 4 pages.
International Application No. PCT/US2016/030365, Written Opinion of the International Searching Authority, dated May 9, 2016, 10 pages.
International Application No. PCT/US2016/030365, International Preliminary Report on Patentability, dated Nov. 7, 2017, 11 pages.
Europe Patent Application No. 16726680.8, Communication pursuant to Rules 161(1) and 162 EPC, dated Dec. 7, 2017.
Europe Patent Application No. 16726680.8, Examination Report, dated Nov. 23, 2018, 8 pages.

* cited by examiner

GAS IDENTIFICATION BY MEASURING STAIN DEVELOPMENT AT MULTIPLE SPECIFIC WAVELENGTH REGIONS WITH NARROW BAND OPTICAL SENSORS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Low concentration gas detectors are typically operable to detect one target gas at a time. Multiple detectors may be available to users working in an area when multiple gasses may be present. Some gas detectors may use color changing indicators operable to react with the target gas, where the color may be monitored either visually by a user or by a light detector.

SUMMARY

Aspects of the disclosure may include embodiments of a gas detector device comprising a wide band light source; at least two narrow band light sensors, wherein each sensor may be operable to detect light at a different range of wavelengths; a color changing indicator operable to react with gas in the air to change color, wherein different gases may react to create different colors, and wherein the sensors detect light reflected by the color changing indicator from the wide band light source; a processor in communication with the at least two light sensors operable to: periodically receive detected reflected wavelength information from the light sensors; relate the detected wavelength to the color for that wavelength range; determine the type of gas that reacted with the color changing indicator based on the color detected by the sensors, wherein each color may be associated with a different type of gas; and determine the concentration of the detected gas based on the rate of change of the color of the color changing indicator.

In some embodiments, the color changing indicator may comprise a stain strip. In some embodiments, the processor may be further operable to communicate the detected gas information. In some embodiments, the color changing indicator may be operable to react with up to five different gases and change to five different colors. In some embodiments, determining the concentration of the detected gas based on the rate of change of the color of the color changing indicator may further comprise measuring the change in the darkness of the color changing indicator. In some embodiments, measuring the change in the darkness of the color changing indicator may comprise measuring, by the light sensors, the intensity of the reflected light from the color changing indicator. In some embodiments, the wide band light source may comprise a wide band Light Emitting Diode (LED). In some embodiments, the at least two narrow band light sensors may comprise a light sensor array, wherein each light sensor detects approximately a 10 nanometer range of wavelengths. In some embodiments, the light sensor array may comprise approximately 9 narrow band light sensors. In some embodiments, the processor may be further operable to determine that the type of gas is a non-target gas or a mixture of gases when the color does not match one of the associated colors.

Additional aspects of the disclosure may include embodiments of a gas detector device comprising: a wide band light-emitting diode (LED); a plurality of narrow band light sensors, wherein each sensor is operable to detect light at a different range of wavelengths; a color changing stain strip operable to react with gas in the air to change color, wherein different gases react to create different colors, and wherein the sensors detect light reflected by the color changing indicator from the wide band light source; a processor in communication with the at least two light sensors operable to: periodically receive detected reflected wavelength information from the light sensors; relate the detected wavelength to the color for that wavelength range; determine the type of gas that reacted with the color changing indicator based on the color detected by the sensors, wherein each color is associated with a different type of gas; and determine the concentration of the detected gas based on the rate of change of the color of the color changing indicator.

In some embodiments, the processor may be further operable to determine that the type of gas is a non-target gas or a mixture of gases when the color does not match one of the associated colors. In some embodiments, the gas detector device may further comprise a memory connected to the processor, wherein the associations between detected color and type of gas may be stored by the memory and accessed by the processor. In some embodiments, the processor may be operable to store information to the memory. In some embodiments, determining the concentration of the detected gas based on the rate of change of the color of the color changing indicator may further comprise measuring the change in the darkness of the color changing indicator.

Other aspects of the disclosure may include embodiments of a method for detecting gas by a gas detector device comprising: providing a color changing indicator operable to react with one of a plurality of gases to change to a color, wherein each color is associated with a type of gas; directing a wide band light source onto the color changing indicator; detecting, by a plurality of light sensors, reflected light from the color changing indicator, wherein the plurality of light sensors are operable to detect light a different ranges of wavelengths; relating the detected reflected light with a color for that wavelength range; determining the type of gas that reacted with the color changing indicator based on the color detected by the light sensors; determining the concentration of the detected gas by measuring the rate-of-change of the darkness of the color changing indicator.

In some embodiments, measuring the darkness of the color changing indicator may comprise measuring, by the light sensors, the intensity of the reflected light from the color changing indicator. In some embodiments, the method may further comprise determining that the type of gas is a non-target gas or a mixture of gases when the color does not match one of the associated colors. In some embodiments, the method may further comprise defining a plurality of gases and the wavelength range associated with that gas, wherein a first gas is associated with a first wavelength range, and a second gas is associated with a second wavelength range. In some embodiments, the color changing indicator may comprise a color stain strip.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
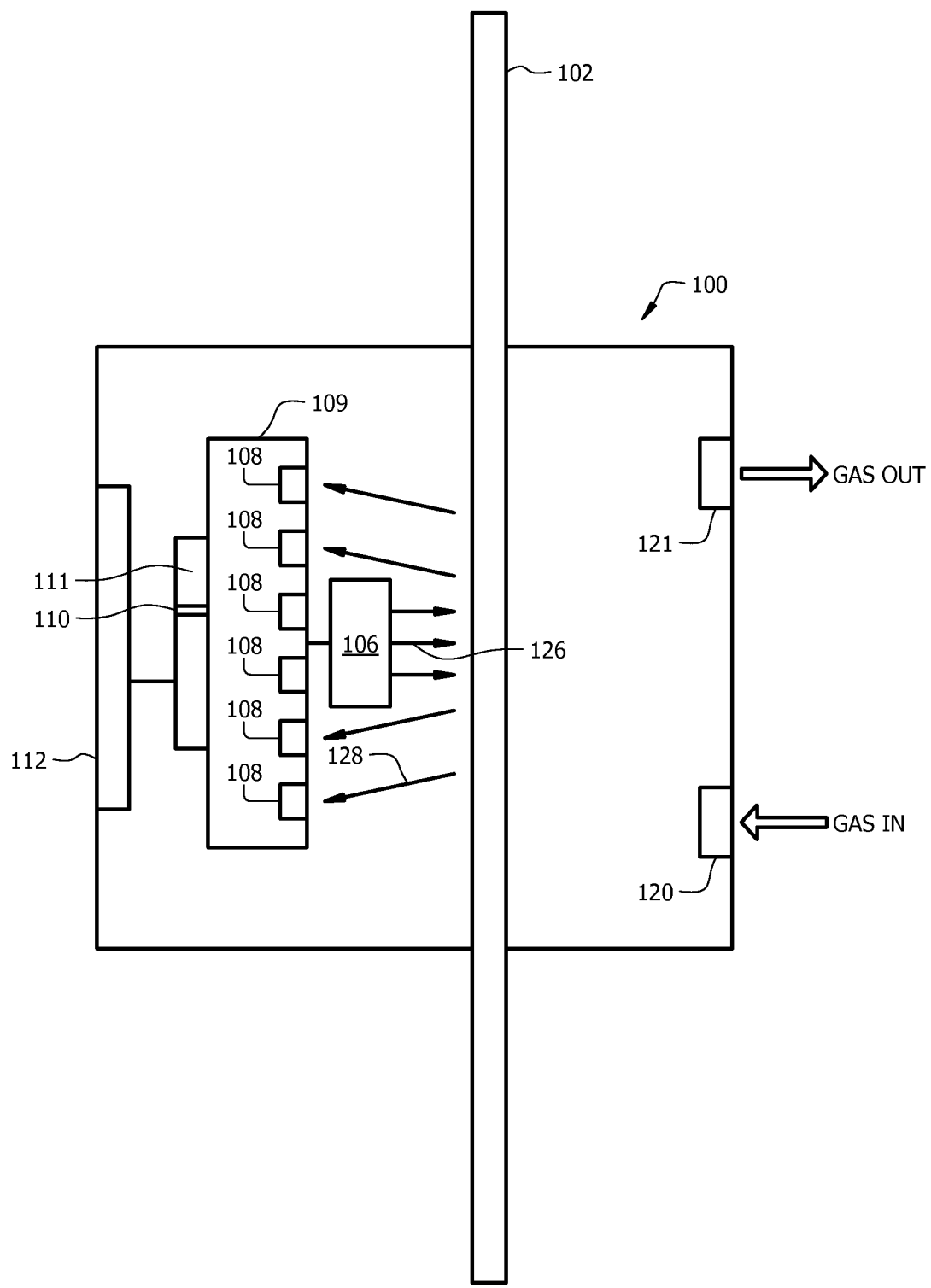
FIG. 1 illustrates a gas detector device according to an embodiment of the disclosure.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Embodiments of the disclosure include systems and methods for detecting gas using a wide band light source, and at least two narrow band light sensors, wherein each sensor may be operable to detect light at a different range of wavelengths. Additionally, the gas detector device may comprise a color changing indicator operable to react with gas in the air to Change color, wherein different gases may react to create different colors, and wherein the sensors detect light reflected by the color changing indicator from the wide band light source. The gas detector device may comprise a processor in communication with the at least two light sensors operable to periodically receive detected reflected wavelength information from the light sensors; relate the detected wavelength to the color for that wavelength range; determine the type of gas that reacted with the color changing indicator based on the color detected by the sensors, wherein each color may be associated with a different type of gas; and determine the concentration of the detected gas based on the rate of change of the color of the color changing indicator.

Referring now to FIG. 1, an exemplary embodiment of a gas detector device 100 is described. The gas detector device 100 may comprises a gas inlet 120 and a gas outlet 121 for allowing gas to flow through the gas detector device 100. The gas detector device 100 may also comprise a color changing indicator 102 that is operable to react with gas entering the device 100 to change to a plurality of colors, wherein each color is associated with a different type of gas. In some embodiments, the color changing indicator 102 may be operable to react with a plurality of gases to change to a plurality of colors. In some embodiments, the color changing indicator 102 may be operable to react with up to five different gases and change to five different colors. In some embodiments, the color changing indicator 102 may comprise a color stain strip (or tape) wherein the strip is treated with a chemical operable to react with the gas(es). In some embodiments, the color changing indicator 102 may be operable to react with multiple gasses within the same family. In some embodiments, the color changing indicator 102 may be removable and may be replaced by another color changing indicator 102, wherein a plurality of color changing indicators 102 (that may be associated with different gas families) may be used with the gas detector device 100.

In some embodiments, the gas detector device 100 may comprise a wide band light source 106 operable to direct light onto the surface of the color changing indicator 102, wherein the light is indicated by arrows 126. The wide band light 106 may emit it light at a wide range of wavelengths. In some embodiments, the wide band light source may comprise a wide band Light Emitting Diode (LED). Also, the gas detector device 100 may comprise a plurality of narrow band light sensors 108 operable to detect light reflected from the surface of the color changing indicator 102, wherein reflected light is indicated by arrows 128. In some embodiments, the light sensors 108 may be housed in an array 109. In some embodiments, each light sensor 108 may be operable to detect light at different ranges of wavelengths, wherein each range of wavelength (or color) may be associated with a type of gas detected by the color changing indicator. In some embodiments, each light sensor 108 is operable to detect approximately a 10 nanometer (nm) range of wavelengths. For example, one light sensor 108 may be operable to detect light at 565±5 nm, while another light sensor 108 may be operable to detect light at 590±5 nm. In other embodiments, the light sensors may be operable to detect light at a wider range of wavelengths, such as 20 nm, 30 nm, 40 nm, 50 100 nm, etc. The range may be chosen based on the application of the gas detector device and the expected colors to be detected by the light sensors. In some embodiments, the light sensor array 109 comprises approximately 9 narrow band light sensors 108. However, any arrangement of light sensors 108 in an array may be used, wherein each light sensor 108 is operable to detect a different range of wavelengths.

In some embodiments, the light sensors 108 may be in communication with a processor 110 operable to receive and process information from the light sensors 108. The processor 110 may be operable to periodically receive detected reflected wavelength information from the light sensors 108, wherein the information may be monitored over time. In some embodiments, the reflected light information may be monitored periodically, such as every one second or every two seconds. The processor 110 may also be connected to a memory 111, wherein the processor 110 may store information to the memory 111 and access information from the memory 111.

The processor 110 may be operable to relate the detected wavelength to the color for that wavelength range, and determine the type of gas that reacted with the color changing indicator 102 based on the color detected by the sensors 108, wherein each color is associated with a different type of gas. In some embodiments, the associations between color and type of gas may be stored in the memory 111. In some embodiments, the processor 110 may be operable to determine the concentration of the detected gas based on the rate of change of the color of the color changing indicator 102. In some embodiments, determining the concentration of the detected gas based on the rate of change of the color of the color changing indicator may comprise measuring the change in the darkness of the color changing indicator 102. Additionally, measuring the change in the darkness of the color changing indicator 102 may comprise measuring, by the light sensors 108, the intensity of the reflected light 128 from the color changing indicator 102.

In some embodiments, the color changing indicator may be operable to react with one gas at a time, wherein if a mixture of gasses enters the gas detector device 100, the color changing indicator may become a color that is not associated with a type of gas. Additionally, if a gas enters the gas detector device 100 that is not anticipated, the color changing indicator may become a color that is not associated with a type of gas. In some embodiments, the processor 110 may be operable to determine that the type of gas detected by the gas detector device 100 is a non-target gas or a mixture of gases when the color does not match one of the associated colors. In some embodiments, the color changing indicator 102 may be operable to react with multiple gases sequentially, but not at the same time (or in a mixture).

In some embodiments, the processor 110 may be further operable to communicate the detected gas information. For example, the gas detector device 100 may comprise a user interface 112, such as a screen, display, lights, or other indicator, wherein the user interface 112 may display information received from the processor 110. In some embodiments, the gas detector device 100 may be wirelessly enabled to communicate information to another device, such as a central monitoring device, Wherein the processor 110 may communicate the processed information received from the light sensors.

Figure 2:
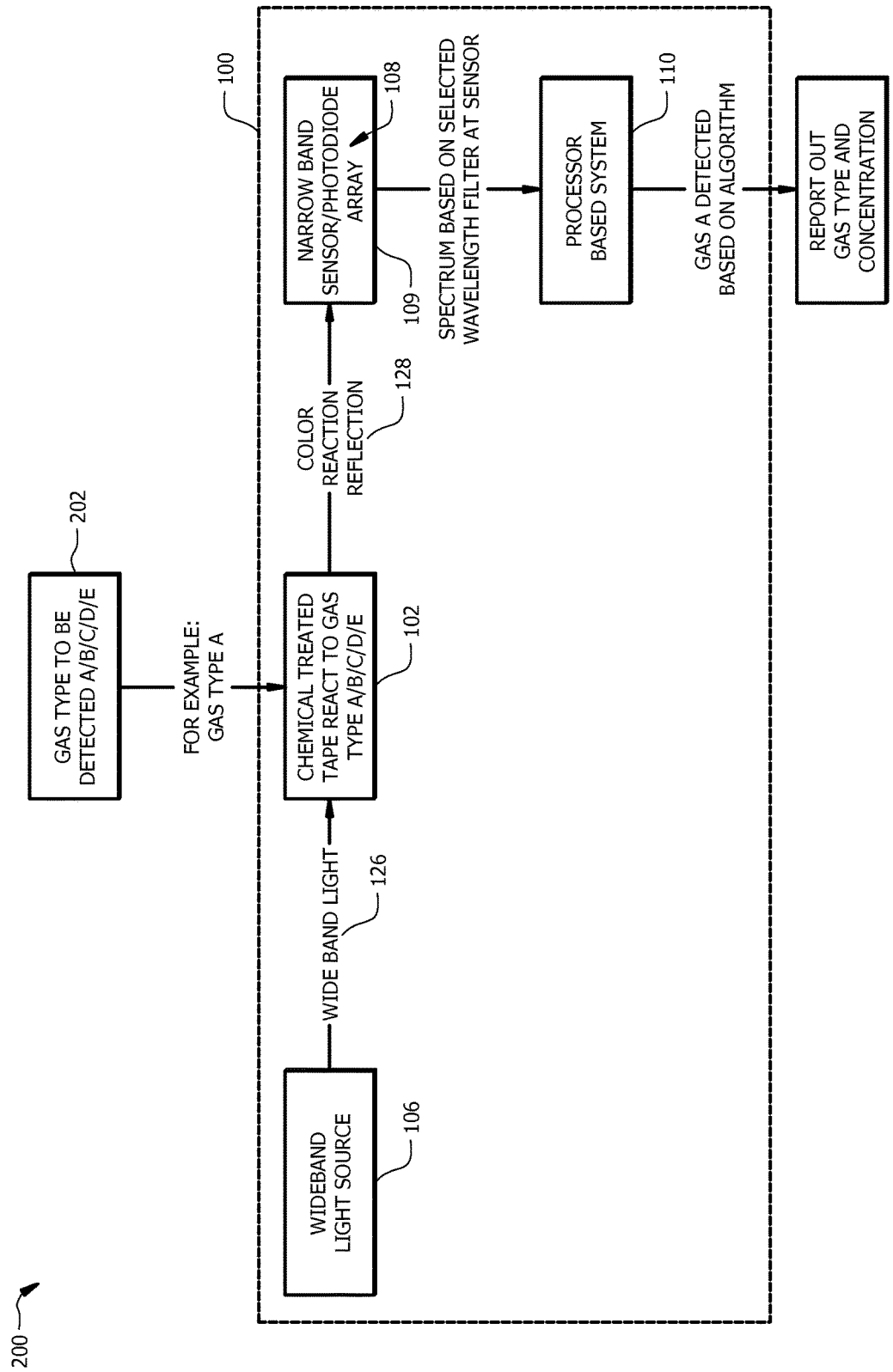
FIG. 2 illustrates a flow chart of a system for detecting gas by a gas detector according to art embodiment of the disclosure.

Referring to FIG. 2, a flow chart 200 for gas detection is shown. In the embodiment shown, a gas 202 that is to be detected may enter the gas detector device 100. The gas 202 may be one of a plurality of gases, indicated by A, B, C, D, or E, wherein each of the gases could react with the color indicator 102 to change the color of the color indicator 102. In the example shown in FIG. 2, the gas 202 is Gas A. Wide band light 126 may be directed onto the color indicator 102 by the wideband light source 106, wherein the color indicator has reacted with the Gas A 202. The reflection light 128 of the color reaction may be detected by the narrow band light sensor 108, which may also be part of a photodiode array 109. The color spectrum of the reflected light 128 may be determined by noting the wavelength of the light sensor 108 that detects the reflected light 128, wherein each of the sensors may comprise a different wavelength filter for a specific range of wavelengths. This information may be communicated to the processor 110, wherein the processor 110 may determine which gas has been detected by accessing an association between the type of gas and the color spectrum information received from the light sensors 108. In some embodiments, the processor 110 may access an algorithm for determining the type of gas from the color spectrum information received from the light sensors 108. In some embodiments, the processor 110 may communicate (or report) the determined gas information as well as the concentration of the detected gas. For example, the information may be displayed on a user interface of the gas detector device 100 and/or communicated to another device, such as a central monitoring station.

Figure 3:
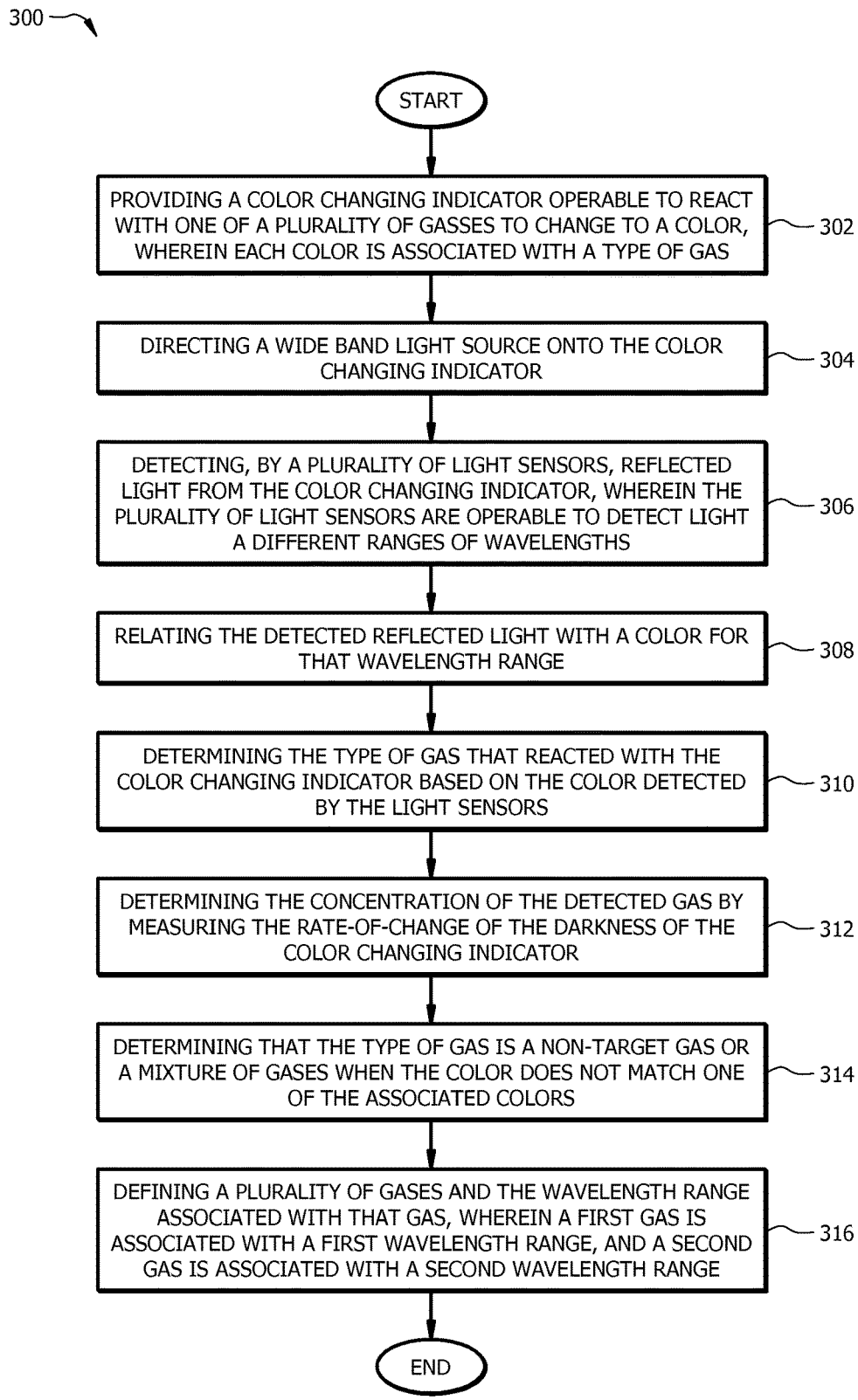
FIG. 3 illustrates a method for detecting gas by a gas detector according to an embodiment of the disclosure.

FIG. 3 illustrates a method 300 for detecting gas by a gas detector device. At step 302, a color changing indicator is provided, wherein the color changing indicator is operable to react with one of a plurality of gases to change to a color, wherein each color is associated with a type of gas. At step 304, a wide band light source is directed onto the color changing indicator. At step 306, reflected light from the color changing indicator is detected by a plurality of light sensors, wherein the plurality of light sensors are operable to detect light a different ranges of wavelengths. At step 308, the detected reflected light is related with a color for that wavelength range. At step 310, the type of gas that reacted with the color changing indicator is determined based on the color detected by the light sensors. At step 312, the concentration of the detected gas is determined by measuring the rate-of-change of the darkness of the color changing indicator, in some embodiments, measuring the darkness of the color changing indicator may comprise measuring, by the light sensors, the intensity of the reflected light from the color changing indicator. In some embodiments, at step 314, the method 300 may optionally comprise determining that the type of gas is a non-target gas or a mixture of gases when the color does not match one of the associated colors. In some embodiments, at step 316, the method 300 may optionally comprise defining a plurality of gases and the wavelength range associated with that gas, wherein a first gas is associated with a first wavelength range, and a second gas is associated with a second wavelength range. In some embodiments, the color changing indicator comprises a color stain strip.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as comprises, includes, and having should be understood to provide support for narrower terms such as consisting of, consisting essentially of, and comprised substantially of. Use of the term "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, Whether electrically, mechanically, or otherwise. Other examples of changes, substitutions, and alterations are ascertainable by one skilled in the art and could be made without departing from the spirit and scope disclosed herein.

What is claimed is:

1. A gas detector device comprising:
   wide band light source;
   a light sensor array comprising at least nine narrow band light sensors, wherein each sensor is configured to detect light at a different range of wavelengths of approximately 10 nanometers;
   a color changing indicator operable to react with gas in air to change color, wherein different gases react to create different colors;
   wherein the wide band light source is configured to direct a wide band light onto the color changing indicator, wherein the wide band light comprises a range of wavelengths that spans the different wavelengths detected by all of the at least nine narrow band light sensors, and
   wherein the sensors are configured to detect a light reflected by the color changing indicator from the wide band light source, and
   a processor in communication with at least two light sensors of the light sensor array configured to:
   periodically receive detected reflected wavelength information from the at least two light sensors;
   relate the detected wavelength to the color for that wavelength range;
   determine a type of gas that reacted with the color changing indicator based on the color detected by the at least two sensors, wherein each color is associated with a different type of gas; and
   determine concentration of the detected gas based on a rate of change of the color of the color changing indicator, wherein determining the concentration of the detected gas based on the rate of change of the color of the color changing indicator further comprises measuring change in darkness of the color changing indicator by measuring intensity of the reflected light from the color changing indicator.

2. The gas detector device of claim 1, wherein the color changing indicator comprises as am strip.

3. The gas detector device of claim 1, wherein the processor is further operable to communicate the detected gas information.

4. The gas detector device of claim 1, wherein the color changing indicator is operable to react with up to five different gases and change to five different colors.

5. The gas detector device of claim 1, wherein the wide band light source comprises a wide band Light Emitting Diode (LED) configured to simultaneously emit light across a range of wavelengths that spans the different wavelengths detected by all of the at least nine narrow band light sensors.

6. The gas detector device of claim 1, wherein the processor is further operable to determine that the type of gas is a non-target gas or a mixture of gases when the color does not match one of the associated colors.

7. A gas detector device comprising:
   a wide band light-emitting diode (LED);
   a light sensor array comprising a plurality of narrow band light sensors, wherein each light sensor is configured to detect light at a different range of wavelengths of approximately 10 nanometers;
   a color changing stain strip operable to react with gas in air to change color, wherein the color changing stain strip is configured such that different gases react to create different colors;
   wherein the wide band LED is configured to direct a wide band light onto the color changing stain strip, wherein the wide band light comprises a range of wavelengths that spans the different wavelengths detected by all of the plurality of narrow band light sensors, and
   wherein the sensors of the light sensor array are configured to detect light reflected by the color changing indicator from the wide band LED, and
   a processor in communication with at least two light sensors of the plurality of narrow band light sensors operable to:
   periodically receive detected reflected wavelength information from the plurality of narrow band light sensors;

relate the detected wavelength to the color for that wavelength range;

determine a type of gas that reacted with the color changing stain strip based on the color detected by the at least two sensors, wherein each color is associated with a different type of gas; and determine a concentration of the detected gas based on a rate of change of the color of the color changing stain strip, wherein determining the concentration of the detected gas based on the rate of change of the color of the color changing stain strip comprises measuring the change in darkness of the color changing stain strip by measuring intensity of the reflected light from the color changing stain strip.

8. The gas detector device of claim 7, wherein the processor is further operable to determine that the type of gas is a non-target gas or a mixture of gases when the color does not match one of the associated colors.

9. The gas detector device of claim 7, further comprising a memory connected to the processor, wherein the associations between detected color and type of gas are by the memory and accessible by the processor.

10. The gas detector device of claim 9, wherein the processor is operable to store information to the memory.

11. A method for detecting gas by a gas detector device comprising:

providing a color changing indicator operable to react with one of a plurality of gases to change to a color, wherein each color is associated with a type of gas;

directing a wide band light source onto the color changing indicator by simultaneously emitting, from a wide band Light Emitting Diode (LED), light across a range of wavelengths that spans all wavelengths detected by a light sensor array comprising a plurality of light sensors;

detecting, by the plurality of light sensors of the light sensor array, reflected light from the color changing indicator, wherein the plurality of light sensors are operable to detect light at different ranges of wavelengths of approximately 10 nanometers;

relating the detected reflected light with a color for that wavelength range;

determining a type of gas that reacted with the color changing indicator based on the color detected by the plurality of light sensors;

determining concentration of the detected gas by measuring a rate-of-change of darkness of the color changing indicator by measuring intensity of the reflected light from the color changing indicator; and wherein the wide band light-emitting diode is configured to direct wide band light onto the color changing indicator.

12. The method of claim 11, further comprising determining that the type of gas is a non-target gas or a mixture of gases when the color does not match one of the associated colors.

13. The method of claim 11, further comprising defining a plurality of gases and the wavelength range associated with each gas, wherein a first gas is associated with a first wavelength range, and a second gas is associated with a second wavelength range.

14. The method of claim 11, wherein the color changing indicator comprises a color stain strip.

* * * * *